US010196660B2

(12) United States Patent
Li et al.

(10) Patent No.: US 10,196,660 B2
(45) Date of Patent: Feb. 5, 2019

(54) **XYLENE MONOOXYGENASE-PRODUCING STRAIN *ARTHROBACTER WOLUWENSIS* AND ITS APPLICATION**

(71) Applicants: Disha Pharmaceutical Group Co., Ltd., Weihai, Shangdong (CN); Weihai Disu Pharmaceutical Co., Ltd., Weihai, Shandong (CN)

(72) Inventors: Guangsheng Li, Shandong (CN); Tao Yang, Shandong (CN); Gangqiang Wan, Shandong (CN); Xinxin Qu, Shandong (CN)

( * ) Notice: Subject to any disclaimer, the term of this patent is extended or adjusted under 35 U.S.C. 154(b) by 0 days.

(21) Appl. No.: 15/573,874

(22) PCT Filed: Aug. 28, 2017

(86) PCT No.: PCT/CN2017/099225
§ 371 (c)(1),
(2) Date: Nov. 14, 2017

(87) PCT Pub. No.: WO2018/045886
PCT Pub. Date: Mar. 15, 2018

(65) Prior Publication Data
US 2018/0346947 A1 Dec. 6, 2018

(30) Foreign Application Priority Data
Sep. 12, 2016 (CN) .......................... 2016 1 0814722

(51) Int. Cl.
*C12P 17/12* (2006.01)
*C12N 9/02* (2006.01)
*C12R 1/06* (2006.01)

(52) U.S. Cl.
CPC ............ *C12P 17/12* (2013.01); *C12N 9/0077* (2013.01); *C12R 1/06* (2013.01); *C12Y 114/15* (2013.01)

(58) Field of Classification Search
None
See application file for complete search history.

(56) References Cited

U.S. PATENT DOCUMENTS

2006/0051782 A1* 3/2006 Wood .................. C12N 9/0069 435/6.18

OTHER PUBLICATIONS

Kutanovas et al., Bioconversion of nnethylpyrazines and pyridines using novel pyrazines-degrading microorganisms, Chemija, 2013, 24, 67-73.*
Genbank, Accession No. KF887413.1, 2014, www.ncbi.nlm.gov.*
Genbank, Accession No. AB244293, 2007, www.ncbi.nlm.gov.*

* cited by examiner

*Primary Examiner* — Robert B Mondesi
*Assistant Examiner* — Todd M Epstein
(74) *Attorney, Agent, or Firm* — Enshan Hong; VLP Law Group LLP

(57) ABSTRACT

The present invention belongs to microbial technology field and relates to a strain producing toluene o-xylene monooxygenase (*Arthrobacter woluwensis*) HW-1 and its application in preparation of 5-methylpyrazine-2-carboxylic acid by microbial fermentation. The present invention providing a new strain HW-1 which could produce toluene o-xylene monooxygenase, and the strain is identified as *Arthrobacter woluwensis*. The strain is firstly found to convert 2, 5-dimethylpyrazine by bio-fermentation to obtain the medicine intermediate 5-methylpyrazine-2-carboxylic acid. The concentration of accumulated product could reach 34.19 g/L and the yield rate is 81.4% by shake flask fermentation. Compared with 20.41 g/L reported in the literature, this method has a greater advantage and could be industrialized. The conditions to prepare 5-methylpyrazine-2-carboxylic acid provided in the present invention is mild, the reaction process is controllable and has good performance in environmental protection and energy saving. So this invention has great value in industry.

9 Claims, 4 Drawing Sheets

Specification includes a Sequence Listing.

SEQUENCE LISTING

```
<160> NUMBER OF SEQ ID NOS: 1

<210> SEQ ID NO 1
<211> LENGTH: 1365
<212> TYPE: DNA
<213> ORGANISM: Arthrobacter woluwensis

<400> SEQUENCE: 1

cagtcgaacg atgaagccta gcttgctggg tggattagtg gcgaacgggt gagtaacacg      60

tgagtaacct gcccttgact ctgggataag cctgggaaac tgggtctaat accggatacg     120

accattgccc gcatgggttg gtggtggaaa gcttttgtgg ttttggatgg actcgcggcc     180

tatcagcttg ttggtgaggt aatggctcac caaggcgacg acgggtagcc ggcctgagag     240

ggtgaccggc cacactggga ctgagacacg gcccagactc ctacgggagg cagcagtggg     300

gaatattgca caatgggcga aagcctgatg cagcgacgcc gcgtgaggga tgacggcctt     360

cgggttgtaa acctctttca gtagggaaga agcgaaagtg acggtacctg cagaagaagc     420

gccggctaac tacgtgccag cagccgcggt aatacgtagg gcgcaagcgt tatccggaat     480

tattgggcgt aaagagctcg taggcggttt gtcgcgtctg ctgtgaaagg ccagggctca     540

accctggttc tgcagtgggt acgggcagac ttgagtgatg taggggagac tggaattcct     600

ggtgtagcgg tgaaatgcgc agatatcagg aggaacaccg atggcgaagg caggtctctg     660

ggcattaact gacgctgagg agcgaaagca tggggagcga acaggattag ataccctggt     720

agtccatgcc gtaaacgttg ggcactaggt gtgggggaca ttccacgttt tccgcgccgt     780

agctaacgca ttaagtgccc cgcctgggga gtacggccgc aaggctaaaa ctcaaaggaa     840

ttgacggggg cccgcacaag cggcggagca tgcggattaa ttcgatgcaa cgcgaagaac     900

cttaccaagg cttgacatgg actggatcgc atcagagatg gtgtttccct tcggggctgg     960

ttcacaggtg gtgcatggtt gtcgtcagct cgtgtcgtga gatgttgggt taagtcccgc    1020

aacgagcgca accctcgttc catgttgcca gcgcgtaatg gcggggactc atgggagact    1080

gccggggtca actcggagga aggtggggac gacgtcaaat catcatgccc cttatgtctt    1140

gggcttcacg catgctacaa tggccggtac aaagggttgc gatactgtga ggtggagcta    1200

atcccaaaaa gccggtctca gttcggattg gggtctgcaa ctcgacccca tgaagttgga    1260

gtcgctagta atcgcagatc agcaacgctg cggtgaatac gttcccgggc cttgtacaca    1320

ccgcccgtca agtcacgaaa gttggtaaca cccgaagccg gtggc                    1365
```

XYLENE MONOOXYGENASE-PRODUCING STRAIN *ARTHROBACTER WOLUWENSIS* AND ITS APPLICATION

PRIORITY CLAIM

This is a U.S. national stage of application No. PCT/CN2017/099225, filed on Aug. 28, 2017. Priority is claimed on the following application: Country: China, Application No.: 201610814722.X, Filed: Sep. 12, 2016, the content of which is incorporated here by reference.

REFERENCE TO SEQUENCE LISTING SUBMITTED VIA EFS-WEB

This application includes an electronically submitted sequence listing in .txt format. The .txt file contains a sequence listing entitled "2018-10-30 6153-2pus_ST25.txt" created on Oct. 30, 2018 and is 2,168 bytes in size. The sequence listing contained in this .txt file is part of the specification and is hereby incorporated by reference herein in its entirety.

TECHNICAL FIELD

This invention relates to microbiology, in particular a strain HW-1 (*Arthrobacter woluwensis*) producing xylene monooxygenase and its application in preparation of 5-Methylpyrazine-2-carboxylic acid by microbial fermentation.

BACKGROUND ART

5-Methylpyrazine-2-carboxylic acid is a beige-white crystalline solid with CAS No. of 5521-55-1, molecular formula of $C_6H_6N_2O_2$, molecular weight of 138.12, and melting point of 166~169° C., has an irritant smell, becomes slowly oxidized when exposed to air, with the appearance turning to a dark viscous solid from brown oil, and therefore needs vacuum preservation.

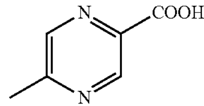

Structural Formula of 5-Methylpyrazine-2-Carboxylic Acid

5-Methylpyrazine-2-carboxylic acid has a wide range of uses in the pharmaceutical industry, is mainly used in the synthesis of hypoglycemic drugs glipizide, new antihypertensive drugs acipimox and antitubercular drug, such as methyl 5-methylpyrazine-2-carboxylate. Therefore, the study in making 5-methylpyrazine-2-carboxylic acid has important value.

The chemical synthesis method of 5-Methylpyrazine-2-carboxylic acid has the following main processes (Chen Binghe, et al. chemical reagents, 2008, 30 (11): 869-870; Dong Yangyang, et al. chemical reagents, 2013, 35 (6), 505~509):

I. 2, 3-two cyano-5-methyl pyrazine is synthesized by cyclization of methylglyoxal and diaminomaleonitrile firstly, and then it is converted to pyrazine-two-carboxylic acid by acid hydrolysis. At last the product is obtained by decarboxylation. Because of the strict conditions of synthesizing diaminomaleonitrile, the expensive import price, and the high toxic. So the cost of this method is high.

II. The method of four steps including chlorination, acylation, hydrolysis and oxidation: 2-methyl-5-chloromethyl pyrazine is obtained by chlorination of 2, 5-Dimethylpyrazine and N-chloroprene two imide initiated by benzoyl peroxide. Then 5-Methylpyrazine-2-carboxylic acid is obtained through acetylation, hydrolysis, and oxidation by potassium permanganate and acidification. The total yield is about 47%. This method takes a long route and is complex, and the total yield rate is low. Potassium permanganate needs to be protected by N2; the waste water contains manganese, is hard to treat and pollutes the environment seriously.

III. Cyclization, oxidation, acidification and decarboxylation method: 2-methyl pyrazine-5, 6-two carboxylic acid is synthesized by cyclization of CIS-2, 3-, two amino-2-butene,-1,4-two nitrile and methylglyoxal and hydrolysis by sulphuric acid. Then 5-methylpyrazine-2-carboxylic acid is obtained through decarboxylation. The route is long and complex. CIS-2, 3-two amino-2-butene-1, 4-two nitrile must be imported, and is very expensive. The mixture of 5-methylpyrazine-2-carboxylic acid and 6-methylpyrazine-2-carboxylic acid obtained by decarboxylation of 2-methyl pyrazine-5, 6-two carboxylic acid is hard to isolate and purify.

IV. Chemical synthetic methods also include intermolecular cyclization, N-Bromo-butadiene-methylene-one-step oxidation method, one step oxidation method of cobalt naphthenate, and electrochemical oxidation method.

Currently, 5-methylpyrazine-2-carboxylic acid is primarily made by chemical methods in industry. But chemical synthesis generally requires high temperature, high pressure, inert gas protection, and the use of a lot of oxidants, therefore producing a lot of waste and pollute environment. And the total yield of chemical synthesis method is low and the cost is high.

Preparation of 5-methylpyrazine-2-carboxylic acid with biological technology has many advantages, such as good substrate selection, high catalytic efficiency, less impurity, and less pollution, which represents the development direction of green chemistry. The Swiss Lonza company has achieved the preparation of 5-methylpyrazine-2-carboxylic acid in batch replenishment reactor using a bacterium containing xylene monooxygenase. Institute of Biology and Environmental engineering, Zhejiang University of Technology (see Yuguo Zheng et al., Chemistry and Bioengierring, 2012, 29(9): 19-25) obtained a xylene monooxygenase-producing strain of *Pseudomonas putida*, and produced 5-methylpyrazine-2-carboxylic acid by using the strain, the fermentation yield reached 75.6% through feed-batch culture. The product concentration reached 20.41 g/L with the period of 22 days.

TECHNICAL PROBLEM

The purpose of the invention is to overcome the deficiency of the chemical synthesis of 5-methylpyrazine-2-carboxylic acid, provide a strain HW-1 with high regioselectivity to catalyze the reaction, and use this strain to prepare 5-methylpyrazine-2-carboxylic acid by fermentation.

TECHNICAL SOLUTION

The technical scheme of the invention is to provide a strain *Arthrobacter woluwensis* HW-1 for producing xylene monooxygenase. This strain was deposited on Aug. 15, 2016 at China General Microbiological Culture Collection Center at No. 1, unit 3, West Beichen Road, Chaoyang District, Beijing, China, with the access number being CGMCC 12833.

The strains in this invention were obtained by the following screening methods:

Soil samples were collected near the sewage outlets of chemical plants from Weihai, Yantai, and Qingdao. Each soil sample was cultured in enrichment medium for three times at 28° C. with shaking at 160 r.p.m. for 48 hours each time. Then the diluted bacteria were coated on the plate medium, and different forms of single colony were picked to inoculate in seed culture medium and coated on the plate medium again, afterwards preserved in refrigerator at 4° C. 0.10 g of 2, 5-dimethylpyrazine was added into fermented liquor after the screened strain was fermented for 12 hours. Centrifugal fermented broth was detected using high-performance liquid chromatography (HPLC) after being incubated for 48 hours. According to the detection result, the strain with highest enzyme activity was obtained, which was named HW-1, and then the strain was identified and subjected to tests for determining optimized fermentation conditions.

The strain provided by the invention has the following taxonomic characteristics:

Colony morphology: After being cultured on plate medium for 48 hours at 28° C., the colony is round, non-folding, edge smooth, glossy, creamy-white and opaque. Colonial morphology is small and short rod in the microscope. Its oxidized form is peroxidase positive.

The 1% agarose gel electrophoresis of PCR products using the extracted total DNA as a template and amplified by the designed primers was performed. As shown in FIG. 1, a fragment of about 1.4 kb was obtained by PCR amplification, which was in accordance with the expected results. The length of the gene fragment was 1365 bp by sequencing.

The similarity analysis between the sequencing gene and the data stored in GenBank showed that the microorganism HW-1 provided by the invention has the highest homology (99%/1365 bps, based on 16S rDNA) with *Arthrobacter woluwensis* (AB244293.1). According to the principle of microbial molecular genetics identification, this strain basically belongs to the control bacteria based on the homology of 16S rDNA sequence more than 95%. Therefore, this strain is identified as *Arthrobacter woluwensis* combined with its physiological and biochemical characteristics and morphology.

The strain provided by the invention may be used for preparing 5-methylpyrazine-2-carboxylic acid, and its characteristics are as following:

The bio-reaction is carried out at 20~40° C., pH 5.0~8.0 with 2-5-dimethylpyrazine as raw material, and the strain HW-1 producing xylene monooxygenase is used as the catalyst, to make 5-methylpyrazine-2-carboxylic acid with a relative high concentration. The product concentration is increased by fed-batch fermentation.

Specific steps are as follows:

Step 1: Preparation of the Seed Culture of the Strain

The *Arthrobacter woluwensis* is inoculated into the seed medium, and cultured in shake flask under the conditions of 100~180 $r \cdot min^{-1}$, 20~40° C. for 12~24 hours. The components of seed medium are 10 g/L of peptone, 5 g/L of yeast extract and 10 g/L of NaCl. The solvent is water.

Step 2: Fermentation and Biotransformation

The seed culture of *Arthrobacter woluwensis* obtained from Step 1 is inoculated into fermentation medium with 1~5% of vaccination quantity and cultured in shake flask with the inducer of xylene for 10~28 hours under the conditions of 100~180 $r \cdot min^{-1}$, pH 6.0~8.0, 20~40° C.

The fermentation medium is induced by xylene and includes other nutrients and trace elements. The components of fermentation medium in this invention are as follows: yeast extract 0.5~2.0 g/L; peptone 1.0~4.0 g/L; $(NH_4)_2SO_4$ 1.0~3.0 g/L; $NaHCO_3$ 1.0~5.0 g/L; $KH_2PO_4$ 0.5~4.0 g/L; NaCl 1.0~5.0 g/L; $MgCl_2$ 0.1~0.5 g/L; $CaCl_2$ 1.0~5.0 g/L; $FeCl_3$ 0.05~0.3 g/L; $ZnSO_4$ 0.02~0.1 g/L; $MnCl_2$ 0.05~0.1 g/L; $CuCl_2$ 0.05~0.02 g/L; $NiCl_2$ 0.01~0.03 g/L; $EDTA.Na_2.2H_2O$ 1.0~5.0 g/L; $FeSO_4$ 1.0~3.0 g/L; the solvent is water.

The process of fermentation and biotransformation can be carried out in a shaker or in a fermentation tank.

2, 5-dimethylpyrazine is added into fermentation, and its initial concentration is 0.5 to 2 mL/L.

The biotransformation from 2, 5-dimethylpyrazine to 5-methylpyrazine-2-carboxylic acid is an acid-forming reaction. In order to increase the reaction rate, pH is adjusted during the conversion to maintain the pH between 6.0 and 7.0.

During the fermentation process, additional 2,5-dimethylpyrazine may be added into fermentation when the conversion rate exceeds 50% according to the results of high-performance liquid chromatography.

Beneficial Results

The beneficial results of the present invention include: a new strain HW-1 is screened which could produce xylene monooxygenase, and it is identified as *Arthrobacter woluwensis*, the strain could be used to convert 2,5-dimethylpyrazine by bio-fermentation to obtain the medicine intermediate, 5-methylpyrazine-2-carboxylic acid. The concentration of accumulated product could reach 34.19 g/L, and the yield rate is 81.4%. Compared with 20.41 g/L reported in the literature, this method has a greater advantage and could be industrialized. The reaction condition is mild, the reaction process is controllable, and the method in accordance with the present invention has good performance in environmental protection and energy saving. Therefore, this invention has great value in industry.

DESCRIPTION OF EMBODIMENTS

EXAMPLE 1

Microbial Screening

Seed culture medium: 5.0 g/L of yeast extract, 10.0 g/L of peptone, 10.0 g/L of NaCl, and the solvent is water and the pH was 7.0.

Enrichment and screening of medium components: yeast extract 1.5 g/L; peptone 2 g/L; $(NH_4)_2SO_4$ 2 g/L; $NaHCO_3$ 1.5 g/L; $KH_2PO_4$ 2 g/L; NaCl 2 g/L; $MgCl_2$ 0.3 g/L; $CaCl_2$ 1.2 g/L; $FeCl_3$ 0.1 g/L; $ZnSO_4$ 0.05 g/L; $MnCl_2$ 0.06 g/L; $CuCl_2$ 0.06 g/L; $NiCl_2$ 0.02 g/L; EDTA.$Na_2$.$2H_2O$ 2 g/L; $FeSO_4$ 1.0~3.0 g/L; xylene was added in an amount of 0.1 mL/L, the solvent is water.

Soil sampling: Soil samples were collected under 5~15 cm deep near the sewage outlet of chemical plant, and acquisition time and place were recorded in details. A total of 100 more soil samples were collected from Weihai, Yantai and Qingdao for screening of objective strains, the differences in geographical distribution of the soil samples could bring more successful opportunities for strains filtration.

Figure 1:
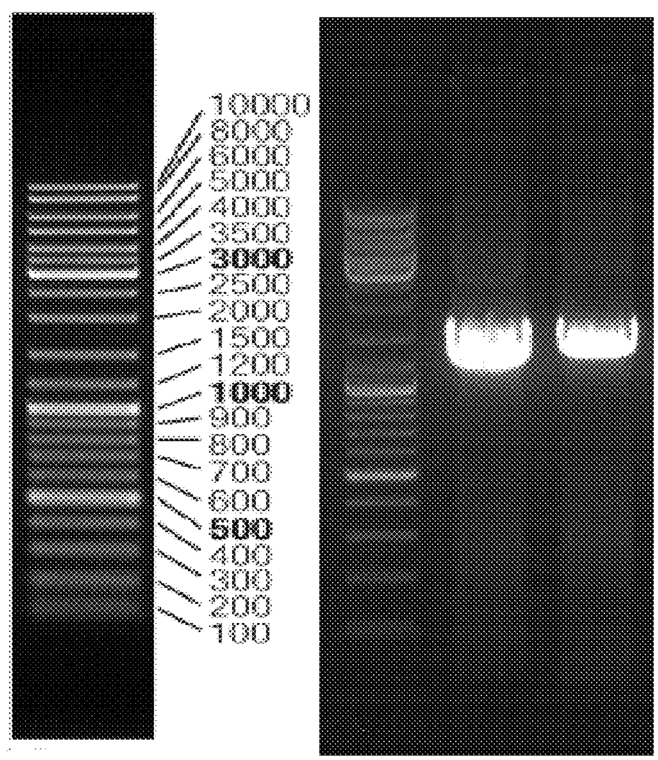
FIG. 1: Agarose gel electrophoresis of the 16S rDNA sequence by PCR amplification of strain HW-1.
Figure 2:
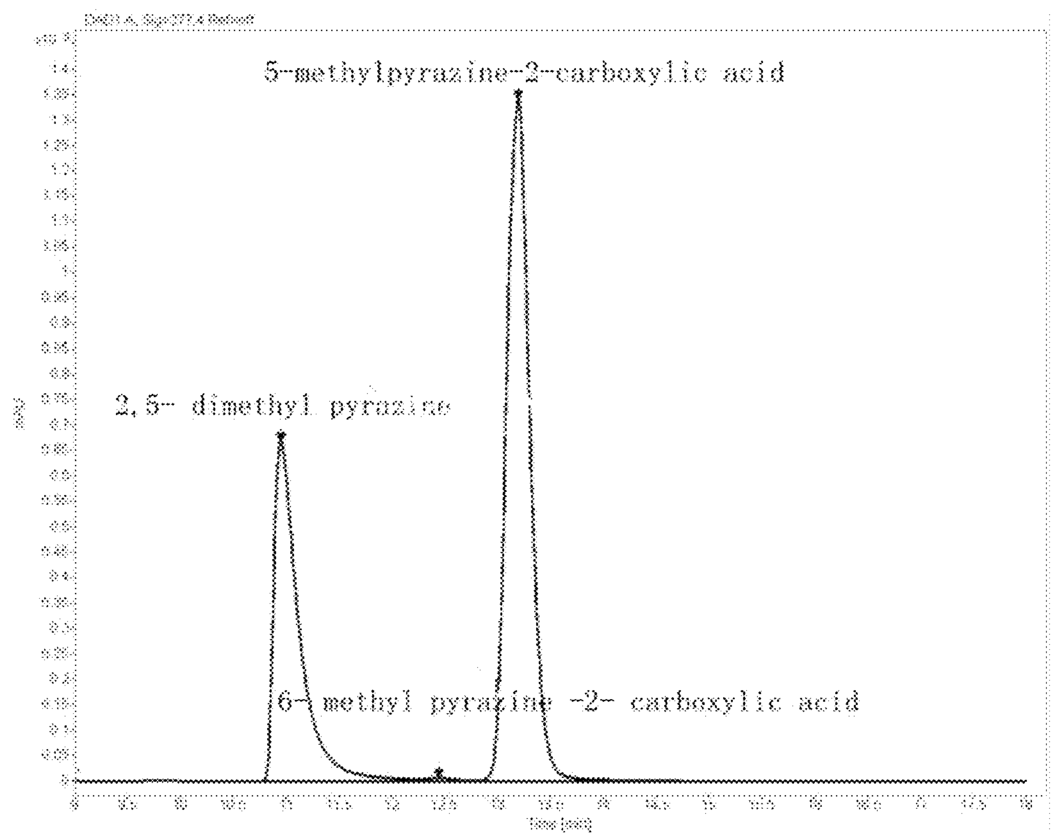
FIG. 2: HPLC chromatogram of the fermentation broth

1 g of soil samples were added into flask and cultured for 40 minutes with addition of 20 mL of saline and glass beads. 0.5 mL of soil suspension was added into the enrichment medium and incubated for 36 h in shaker at 30° C. and 150 $r{\cdot}min^{-1}$. This operation was repeated three times. 0.1 mL of the culture liquid was coated on the solid plate for isolation and growing into single colony at 28° C. The components of solid plate culture medium were as follows: yeast extracts 5.0 g/L, peptone 10.0 g/L, NaCl 5.0 g/L, agar 20 g/L, pH 7.0, and the solvent was water. Single colony was then taken into seed culture medium, and cultured in 150 $r{\cdot}min^{-1}$ shaker at 28° C. for 16 hours to obtain the seed liquid of pure strain. The seed liquid was inoculated into the fermentation medium with 2% vaccination quantity, and incubated in 150 $r{\cdot}min^{-1}$ shaker for 16 h at 28° C. Adding 0.20 g of 2, 5-dimethylpyrazine into fermented liquor after the screened strain fermented for 12 hours. Fermentation liquor was detected by using high-performance liquid chromatography (Column: $C_{18}$ column, acetonitrile:water:trifluoroacetic acid=12:88:0.5, flow rate 1 mL/min, detection wavelength 270 nm, column temperature 25° C.) after fermented for another 36 hours. FIG. 2 is the HPLC chromatogram. According to the detection result, HW-1 strain with the highest enzyme activity (Deposit No. CGMCC12833) was obtained.

EXAMPLE 2

Fermentation Process

The single colony was inoculated into the seed medium and cultured in 150 $r{\cdot}min^{-1}$ shaker for 16 h at 28° C. to obtain the seed liquid of the pure strain. The period of 3 to 16 hours among culture process was the logarithmic period, so this period was the best time to inoculate.

Figure 3:
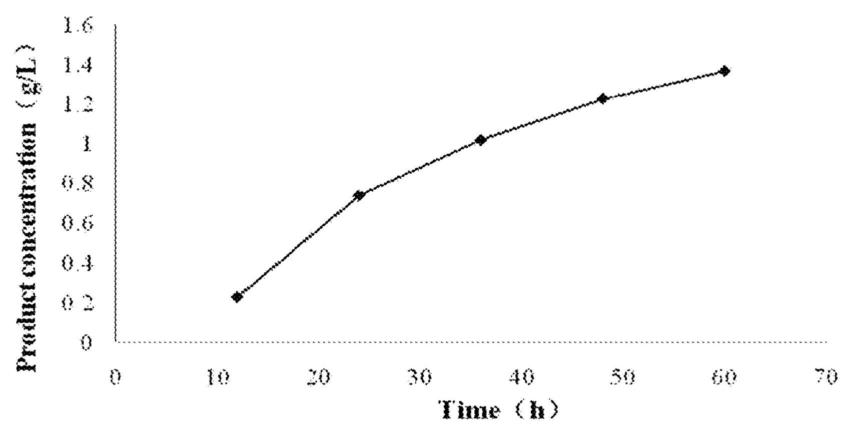
FIG. 3: Accumulation concentration of 5-methylpyrazine-2-carboxylic acid during the fermentation process.

The seed liquid was inoculated into the fermentation medium with 2% vaccination quantity, and incubated in 150 $r{\cdot}min^{-1}$ shaker for 12 h at 28° C. Then 0.20 g of 2, 5-dimethylpyrazine was added into fermentation liquor. The pH of the fermentation liquor was decreasing during the fermentation process and the pH was reduced to 5.1 at 46 hours, and the rate of fermentation was decreased too. During the fermentation process, the concentration of the product was continuously accumulated, and the specific trend was shown in FIG. 3.

EXAMPLE 3

Effect Of Initial pH On Fermentation And Biotransformation

Figure 4:
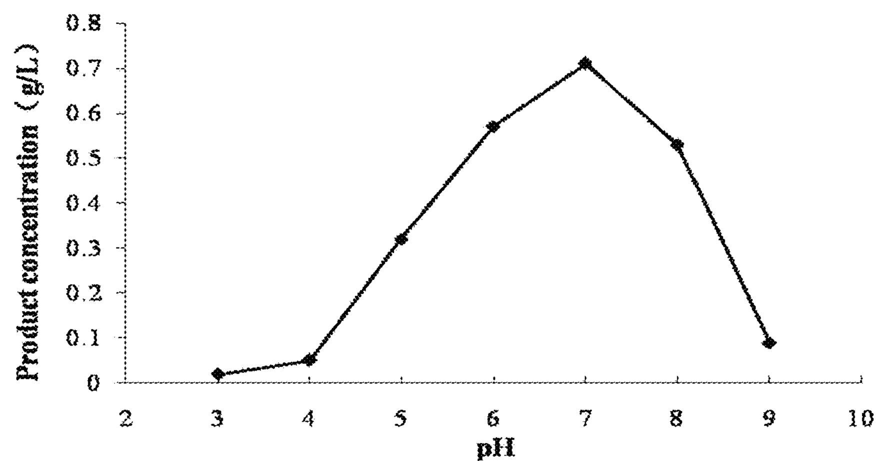
FIG. 4: Effect of initial pH on fermentation and biotransformation.

Fermentation mediums were prepared with different initial pH which were 3.0, 4.0, 5.0, 6.0, 7.0, 8.0 and 9.0, respectively. The seed liquid was inoculated into the fermentation medium with 2% vaccination quantity, and incubated in 150 $r{\cdot}min^{-1}$ shaker for 12 h at 28° C. Then 0.20 g of 2, 5-dimethylpyrazine was added into fermentation liquor. Fermentation liquor was detected after cultured for another 36 hours. The results were shown in FIG. 4. Too high or low pH was bad for the normal growth and metabolism of strains, and also affected the fermentation conversion efficiency. A pH around 7.0 was the best for enhancing the conversion activity and efficiency.

EXAMPLE 4

Effect Of Substrate Amount On Fermentation And Biotransformation

Figure 5:
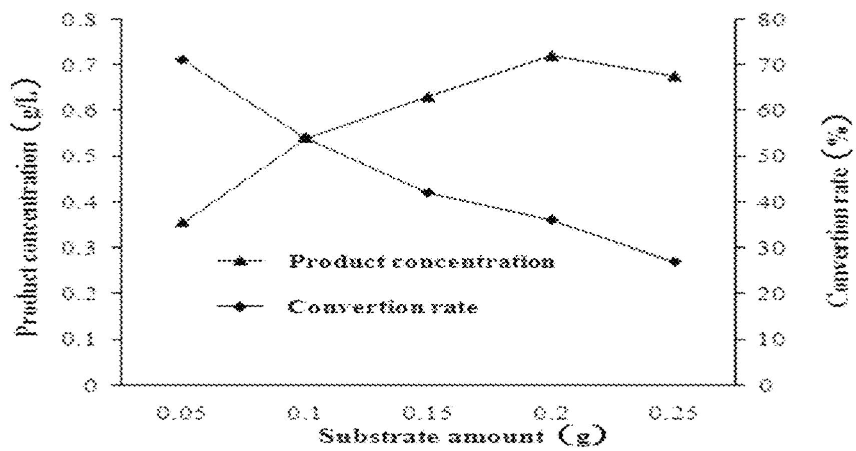
FIG. 5: Effect of the amount of substrate on the transformation (◆ represents conversion rate, ▲ represents accumulation concentration of 5-methylpyrazine-2-carboxylic acid.

The seed liquid was inoculated into 100 mL fermentation medium with 2% vaccination quantity, and incubated in 150 $r{\cdot}min^{-1}$ shaker for 12 h at 28° C. Then 2, 5-dimethylpyrazine was added into fermentation liquor. The additions were 0.05 g, 0.10 g, 0.15 g, 0.20 g and 0.25 g, respectively. Centrifugal fermentation liquor was detected by HPLC to analyze the concentration of 5-methylpyrazine-2-carboxylic acid after cultured for another 36 hours. The results were shown in FIG. 5. The conversion rate was decreased with the addition of substrate 2, 5-dimethylpyrazine increasing, while the concentration of 5-methylpyrazine-2-carboxylic acid in fermentation was increased. The amount of 2, 5-dimethylpyrazine exceeded 0.20 g, substrate inhibition was evident, and it led to the decrease of conversion efficiency and product concentration.

EXAMPLE 5

Effects Of Addition Time Of Substrate On The Transformation

Figure 6:
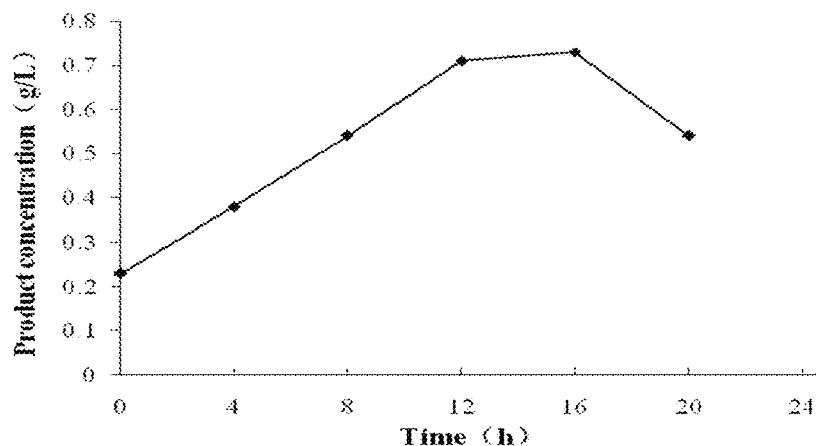
FIG. 6: Effect of substrate addition time on transformation.

The seed liquid was inoculated into 100 mL fermentation medium with 2% vaccination quantity, and incubated in 150 $r{\cdot}min^{-1}$ shaker for 12 h at 28° C. Then 2, 5-dimethylpyrazine was added into fermentation liquor. The addition time were after 0 hour, 4 hours, 8 hours, 12 hours, 16 hours and 20 hours, respectively. Centrifugal fermentation liquor was detected by HPLC to analyze the concentration of 5-methylpyrazine-2-carboxylic acid after cultured for another 36 hours. The results were shown in FIG. 6. The suitable substrate addition time was 12 to 16 hours.

EXAMPLE 6

Effect Of Fermentation And Conversion Temperature On Transformation

Figure 7:
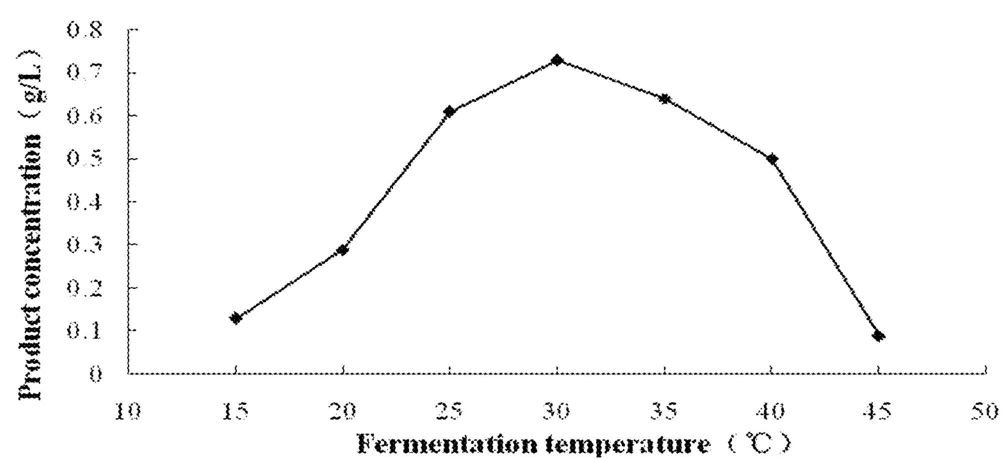
FIG. 7: Effect of fermentation and conversion temperature on transformation.

The seed liquid was inoculated into 100 mL fermentation medium and incubated in 150 $r{\cdot}min^{-1}$ shaker for 12 h. Then 0.20 g of 2, 5-dimethylpyrazine was added into fermentation liquor. The fermentation temperatures were 15° C., 20° C., 25° C., 30° C., 35° C., 40° C. and 45° C., respectively. Centrifugal fermentation liquor was detected by HPLC to analyze the concentration of 5-methylpyrazine-2-carboxylic acid after cultured for another 36 hours. The results were shown in FIG. 7. The suitable substrate fermentation temperature was between 25° C. to 35° C.

EXAMPLE 7

Additional Substrate Conversion

The seed liquid was inoculated into 100 mL fermentation medium and incubated in 150 $r{\cdot}min^{-1}$ shaker for 12 h at 28°

C. Then 0.20 g of 2, 5-dimethylpyrazine was added into the fermentation liquor. According to the product and substrate concentration, 0.20 g of substrate 2, 5-dimethylpyrazine was added into the fermentation after a period of transformation. The transformation process took 372 hours and needed 21 substrate additions. The concentration of 5-methylpyrazine-2-carboxylic acid reached 34.19 g/L, and the yield was 81.4%.

INDUSTRY PRACTICAL APPLICABILITY

A new strain which could produce xylene monooxygenase was screened, and identified as *Arthrobacter woluwensis*. This strain could be used to convert 2,5-dimethylpyrazine by bio-fermentation to obtain the pharmaceutical intermediate, 5-methylpyrazine-2-carboxylic acid. The concentration of the accumulated product could reach 34.19 g/L, and the yield rate was 81.4%. Compared with 20.41 g/L reported in the literature, this method has a greater advantage and could be industrialized. This strain could convert 2,5-dimethylpyrazine to 5-methylpyrazine-2-carboxylic continuously and stably, and the reaction condition is mild, and the reaction process is controllable. Compared with the traditional chemical method, this method has the advantages of high specificity, low by-product, high yield, low energy consumption, environmental protection and energy saving. So this invention has great value in industry.

Gene sequence table (SEQ ID NO: 1)

```
CAGTCGAACG ATGAAGCCTA GCTTGCTGGG TGGATTAGTG GCGAACGGGT GAGTAACACG   060

TGAGTAACCT GCCCTTGACT CTGGGATAAG CCTGGGAAAC TGGGTCTAAT ACCGGATACG   120

ACCATTGCCC GCATGGGTTG GTGGTGGAAA GCTTTTGTGG TTTTGGATGG ACTCGCGGCC   180

TATCAGCTTG TTGGTGAGGT AATGGCTCAC CAAGGCGACG ACGGGTAGCC GGCCTGAGAG   240

GGTGACCGGC CACACTGGGA CTGAGACACG GCCCAGACTC CTACGGGAGG CAGCAGTGGG   300

GAATATTGCA CAATGGGCGA AAGCCTGATG CAGCGACGCC GCGTGAGGGA TGACGGCCTT   360

CGGGTTGTAA ACCTCTTTCA GTAGGGAAGA AGCGAAAGTG ACGGTACCTG CAGAAGAAGC   420

GCCGGCTAAC TACGTGCCAG CAGCCGCGGT AATACGTAGG GCGCAAGCGT TATCCGGAAT   480

TATTGGGCGT AAAGAGCTCG TAGGCGGTTT GTCGCGTCTG CTGTGAAAGG CCAGGGCTCA   540

ACCCTGGTTC TGCAGTGGGT ACGGGCAGAC TTGAGTGATG TAGGGGAGAC TGGAATTCCT   600

GGTGTAGCGG TGAAATGCGC AGATATCAGG AGGAACACCG ATGGCGAAGG CAGGTCTCTG   660

GGCATTAACT GACGCTGAGG AGCGAAAGCA TGGGGAGCGA ACAGGATTAG ATACCCTGGT   720

AGTCCATGCC GTAAACGTTG GGCACTAGGT GTGGGGGACA TTCCACGTTT TCCGCGCCGT   780

AGCTAACGCA TTAAGTGCCC CGCCTGGGGA GTACGGCCGC AAGGCTAAAA CTCAAAGGAA   840

TTGACGGGGG CCCGCACAAG CGGCGGAGCA TGCGGATTAA TTCGATGCAA CGCGAAGAAC   900

CTTACCAAGG CTTGACATGG ACTGGATCGC ATCAGAGATG GTGTTTCCCT TCGGGGCTGG   960

TTCACAGGTG GTGCATGGTT GTCGTCAGCT CGTGTCGTGA GATGTTGGGT TAAGTCCCGC  1020

AACGAGCGCA ACCCTCGTTC CATGTTGCCA GCGCGTAATG GCGGGGACTC ATGGGAGACT  1080

GCCGGGGTCA ACTCGGAGGA AGGTGGGGAC GACGTCAAAT CATCATGCCC CTTATGTCTT  1140

GGGCTTCACG CATGCTACAA TGGCCGGTAC AAAGGGTTGC GATACTGTGA GGTGGAGCTA  1200

ATCCCAAAAA GCCGGTCTCA GTTCGGATTG GGGTCTGCAA CTCGACCCCA TGAAGTTGGA  1260

GTCGCTAGTA ATCGCAGATC AGCAACGCTG CGGTGAATAC GTTCCCGGGC CTTGTACACA  1320

CCGCCCGTCA AGTCACGAAA GTTGGTAACA CCCGAAGCCG GTGGC                  1365
```

The invention claimed is:

1. A method of preparing 5-methylpyrazine-2-carboxylic acid comprising subjecting 2,5-dimethylpyraine as a starting material to fermentation reaction in the presence of a xylene monooxygenase-producing strain *Arthrobacter woluwensis* HW-1 deposited at China General Microbiological Culture Collection Center with access number CGMCC 12833 as a catalyst.

2. The method of claim 1 wherein the fermentation reaction is carried out at 20~40° C., pH 5.0~8.0.

3. The method of claim 2 wherein the pH value is maintained between 6.0 and 7.0 during the fermentation reaction.

4. The method of claim 1 wherein additional 2-5-dimethylpyrazine is fed during the fermentation reaction by fed-batch to increase concentration of 5-methylpyrazine-2-carboxylic acid.

5. The method of claim 4 wherein the additional 2-5-dimethylpyrazine is fed into fermentation when the staring material 2-5-dimethylpyrazine has a conversion rate of greater than 50%.

6. The method of claim 1 comprising preparing a seed liquid of the strain *Arthrobacter woluwensis* HW-1 prior to the fermentation reaction.

7. The method of claim 6 wherein the preparing of the seed liquid of the strain *Arthrobacter woluwensis* HW-1 comprises: inoculating the strain *Arthrobacter woluwensis* HW-1 into a seed medium comprising 10 g/L of peptone, 5 g/L of yeast extract, 10 g/L of NaCl, and water as a solvent, and culturing the strain *Arthrobacter woluwensis* HW-1 in a shake flask under conditions of 100~180 $r \cdot min^{-1}$, 20~40° C. for 12~24 hours.

8. The method of claim 6 comprising prior to the fermentation reaction, inoculating the seed liquid of the strain *Arthrobacter woluwensis* HW-1 in a fermentation medium and culturing the strain *Arthrobacter woluwensis* HW-1 in a shake flask in the presence of xylene as an inducer for 10~28 hours under conditions of 100~180 r·min−1, pH 6.0~8.0, 20~40° C., wherein the fermentation medium comprises: yeast extract 0.5~2.0 g/L; peptone 1.0~4.0 g/L; $(NH_4)_2SO_4$ 1.0~3.0 g/L; $NaHCO_3$ 1.0~5.0 g/L; $KH_2PO_4$ 0.5~4.0 g/L; NaCl 1.0~5.0 g/L; $MgCl_2$ 0.1~0.5 g/L; $CaCl_2$ 1.0~5.0 g/L; $FeCl_3$ 0.05~0.3 g/L; $ZnSO_4$ 0.02~0.1 g/L; $MnCl_2$ 0.05~0.1 g/L; $CuCl_2$ 0.05~0.02 g/L; $NiCl_2$ 0.01~0.03 g/L; EDTA.$Na_2$.2$H_2O$ 1.0~5.0 g/L; $FeSO_4$ 1.0~3.0 g/L; xylene 0.1-2 mL/L, and water as a solvent.

9. The method of claim 8 comprising adding 2, 5-dimethylpyrazine into the fermentation medium at an initial concentration of 0.5 to 2 mL/L.

* * * * *